US007977042B2

(12) United States Patent
Lee et al.

(10) Patent No.: US 7,977,042 B2
(45) Date of Patent: Jul. 12, 2011

(54) COMPOSITION AND METHOD FOR THE RESTORATION AND PRESERVATION OF TRANSPLANT ORGANS PROCURED FROM DCD DONORS

(75) Inventors: Charles Y. Lee, Charlotte, NC (US); Mark G. Clemens, Cornelius, NC (US); Jian X. Zhang, Charlotte, NC (US); Shailendra Jain, Charlotte, NC (US)

(73) Assignee: University of North Carolina at Charlotte, Charlotte, NC (US)

(*) Notice: Subject to any disclaimer, the term of this patent is extended or adjusted under 35 U.S.C. 154(b) by 1384 days.

(21) Appl. No.: 11/460,261

(22) Filed: Jul. 27, 2006

(65) Prior Publication Data

US 2007/0026376 A1    Feb. 1, 2007

Related U.S. Application Data

(60) Provisional application No. 60/702,597, filed on Jul. 27, 2005, provisional application No. 60/739,886, filed on Nov. 28, 2005.

(51) Int. Cl.
*A01N 1/00* (2006.01)
(52) U.S. Cl. ......................................................... 435/1.2
(58) Field of Classification Search .................. None
See application file for complete search history.

(56) References Cited

U.S. PATENT DOCUMENTS

| | | |
|---|---|---|
| 4,798,824 A | 1/1989 | Belzer et al. |
| 4,873,230 A | 10/1989 | Belzer et al. |
| 4,879,283 A | 11/1989 | Belzer et al. |
| 5,693,462 A | 12/1997 | Raymond |
| 5,952,322 A | 9/1999 | Hoover et al. |
| 6,080,730 A | 6/2000 | Lemasters et al. |
| 6,544,726 B1 | 4/2003 | Van Dyke et al. |
| 6,673,594 B1 | 1/2004 | Owen et al. |
| 6,794,124 B2 | 9/2004 | Steen |
| 6,924,267 B2 | 8/2005 | Daemen et al. |
| 7,014,990 B2 | 3/2006 | Polyak et al. |
| 2003/0039638 A1 | 2/2003 | Bach et al. |

FOREIGN PATENT DOCUMENTS

WO    WO 02/30193    4/2002

OTHER PUBLICATIONS

Bessems et al., "Machine Perfusion Preservation of the Non-Heart Beating Donor Rat Livers Using Polysol, A New Preservation Solution," *Transplantation Proceedings*, vol. 37, No. 1, pp. 326-328, Jan. 2005.
Ohwada, et al., "Advantages of Celsior Solution in Graft Preservation from Non-Heart-Beating Donors in a Canine Liver Transplantation Model," *Journal of Surgical Research*, vol. 102, No. 2, pp. 71-76, Feb. 2002.
Tojimbara et al., "Effect of Sodium Lactobionate Sucrose Solution on the Function of Liver Grafts from Non-Heart-Beating Pig Donors," *Transplantation Proceedings*, vol. 33, No. 1-2, pp. 889-890, Feb. 2001.
Barros-Schelotto et al., "Reduced Reperfusion Injury by Glycine in a Porcine Liver Transplantation Model with Non-Heart-Beating Donors," *Transplantation Proceedings*, vol. 34, No. 4, pp. 1114-1117, Jun. 2002.
PCT Search Report and Written for PCT/US2006/029723 dated Jan. 21, 2008.
Minor et al., "Preservation of livers from non-heart beating donors: modulation of cAMP signal and organ viability by glucagons," *Transplant Proc*, 1999; 31(1): 1068.
Lee et al., "Survival Transplantation of Preserved Non-Heart-Beating Donor Rat Livers: Preservation by Hypothermic Machine Perfusion," *Transplantation*, vol. 76, No. 10, pp. 1432-1436, Nov. 2003.
Lee et al., "Functional Recovery of Preserved Livers Following Warm Ischemia: Improvement by Machine Perfusion of Preservation," *Transplantation*, vol. 74, No. 7, pp. 944-951, Oct. 15, 2002.
Acierno et al., "Mathematician, Physicist," *Physiologist. Clin Cardio*, 2000; 23 (5): 390-391.
Daemen et al., "Non-heart-beating donor program contributes 40% of kidneys for transplantation," *Transplant Proc*, Feb. 1996; 28(1): 105-106.
Daemen et al., "The potential pool of non-heart-beating kidney donors," *Clin Transplant*, 1997; 11 (2): 149-154.
Kootstra et al., "The non heart-beating donor," *Br Med Bull*, 1997; 53 (4): 844-853.
Gomez et al., "Liver transplantation with organs from non-heart-beating donors," *Transplant Proc*, 1997; 29 (8): 3478-3479.
D'Alessandro et al., "Successful extrarenal transplantation from non-heart-beating donors," *Transplanation*, Apr. 1995; 59 (7): 977-982.
Casavilla et al., "Experience with liver and kidney allografts from non-heart-beating donors," *Transplanation*, Jan. 1995; 59 (2): 197-203.
Reich et al, "Controlled non-heart-beating donor liver transplantation: a successful single center experience, with topic update," *Transplantation*, Oct. 2000; 70 (8): 1159-1166.
Yamauchi et al., "Warm preflush with streptokinase improves microvascular procurement and tissue integrity in liver graft retrieval from non-heart-beating donors," *Transplantation*, May 2000; 69 (9): 1780.
Tojimbara et al., "Orthotopic liver transplantation from non-heart-beating donor rats: effect of flushing with cold/warm UW/SLS preservation solutions," *Transplant Proc*, 1997: 29 (1-2): 1371-1373.
Takada et al., "Prolonged hepatic warm ischemia in non-heart-beating donors: protective effects of FK506 and a platelet activating factor antagonist in porcine liver transplanation," *Surgery*, Jun. 1998; 123 (6): 692-698.

(Continued)

*Primary Examiner* — Michael Burkhart
(74) *Attorney, Agent, or Firm* — Alston & Bird LLP

(57) ABSTRACT

The present invention provides a perfusion solution comprising specific metabolic agents, antioxidant agents, and membrane stabilizer agents that can help improve preservation, organ viability, and in some cases recover organs that would otherwise being unusable for transplantation. In a further embodiment, the perfusion solution can be used in combination with hypothermic machine perfusion. It has been found that combination of the perfusion solution and hypothermic machine perfusion can help prevent or reduce further damage to the organ and restore the organ's anti-oxidant system, stabilize the cellular cytoskeleton and cellular membranes, inhibit arachidonic acid pathway, provide oncotic support, reduce interstitial edema formation, and help restore energy stores within the organ. As a result, the method can be used to improve the viability of otherwise marginal donor organs.

16 Claims, 1 Drawing Sheet

OTHER PUBLICATIONS

Figure 1:
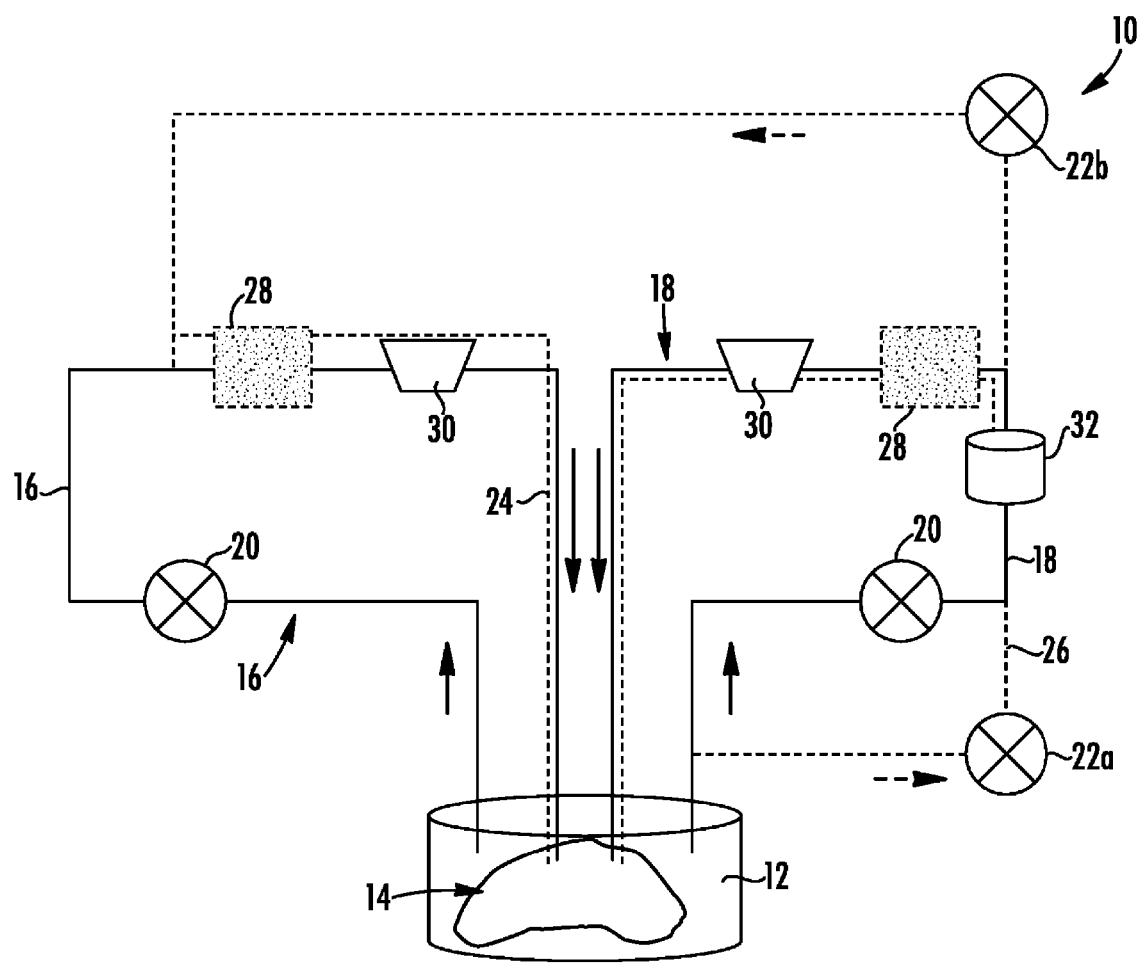

Richter et al., "Effect of warm ischemia time and organ perfusion technique on liver microvascular preservation in a non-heart-beating rat model," *Transplanation*, Jan. 2000; 69 (1): 20.

Kievit et al., "Outcome of machine-perfused non-heart-beating donor kidneys, not allocated within the Eurotransplant area," *Transpl Int*, 1998; 11 Suppl 1: S421-S423.

Daemen et al., "Effect of machine perfusion preservation on delayed graft function in non-heart-beating donor kidneys—early results," *Transpl Int*, 1997; 10 (4): 317-322.

Rizvi, "Non-heart-beating donor transplantation: machine perfusion preservation is the answer to prolonged cold ischemia time," *Transplant Proc*, 2000; 32 (1): 143.

Matsuno et al., "Usefulness of machine perfusion preservation of non-heart-beating donors in kidney transplantation," *Transplant Proc*, Jun. 1996; 28 (3): 1551-1552.

Balupuri et al., "The trouble with kidneys derived from the non-heart-beating donor: a single center 10-year experience," *Transplantation*, Mar. 2000: 69 (5): 842-846.

Daemen et al., "Short-term outcome of kidney transplants from non-heart-beating donors after preservation by machine perfusion," *Transpl Int*, 1996; 9 Suppl 1: S76-S80.

Iwamoto et al., "Beneficial effect of machine perfusion preservation on liver transplantation from non-heart-beating donors," *Transpl Proc* 2000; 32 (7); 1645-1646.

Uchiyama et al., "Liver transplantation from non-heart-beating donors: effect of machine perfusion preservation and pentoxifylline," *Transplant Proc*, 1998; 30 (7): 3798-3800.

Kozaki et al., "Usefulness of a combination of machine perfusion and pentoxifylline for porcine liver transplantation from non-heart-beating donors with prolonged hypotension," *Transplant Proc*, 1997; 29 (8): 3476-3477.

Jaeschke, "Mechanisms of reperfusion injury after warm ischemia of the liver," *J Hepatobiliary Pancreat Surg*, Mar. 1998; 5 (4): 402-408.

Jamieson et al., "Preservation of the canine liver for 24-48 hours using simple cold storage with UW solution," *Transplantation*, Oct. 1998; 46 (4): 517-522.

Zimmerman et al., "Mechanisms of reperfusion injury," *Am J Med Sci*, Apr. 1994; vol. 307, No. 4, 284-292.

Borghi et al., "Apoptosis after ischemia-reperfusion in human liver allografts," *Liver Transpl Surg*, Jul. 1997; 3 (4): 407-415.

Jaeschke et al., "Neutrophil and Kupffer cell-induced oxidant stress and ischemia-reperfusion injury in rate liver," 1991; 260 (3 Pt 1): G355-G362.

Pannen et al., "Role of endothelins and nitric oxide in hepatic reperfusion injury in the rat," Mar. 1998; 27 (3): 755-764.

Goto et al., "Endothelin-1 is involved in the pathogenesis of ischemia/reperfusion liver injury by hepatic microcirculatory disturbances," 1994; 19 (3): 675-681.

Hisama et al., "Kupffer cell production of cytokine-induced neutrophil chemoattractant following ischemia/reperfusion injury in rats," *Hepatology*, Nov. 1996; 24 (5): 1193-1198.

Wanner et al., "Liver ischemia and reperfusion induces a systemic inflammatory response through Kupffer cell activation," *Shock*, Jan. 1996; 5 (1): 34-40.

Clemens et al., "Remodeling of hepatice mircovascular responsiveness after ischemia/reperfusion," *Shock*, Aug. 1997; 8 (2): 80-85.

Garcia-Pagán et al., "Ischemia/reperfusion induces an increase in the hepatic portal vasoconstrictive response to endothelin-1," *Shock*, 1999; 11 (5): 325-329.

Gao et al., "Apoptosis of sinusoidal endothelial cells is a critical mechanism of preservation injury in rat liver transplantation," *Hepatology*, Jun. 1998; 27 (6): 1652-1660.

Belzer et al., "Principles of Solid-Organ Preservation by Cold Storage" *Transplantation*, Apr. 1998; 45: 673-676.

D'Alessandro et al., "Solution development in organ preservation: The University of Wisconsin Perspective," *Transplantation Review*, 1999; 13 (2): 67-77.

Southard et al., "Organ preservation," *Annu Rev Med*, 1995; 46: 235-247.

Changani et al., "Hepatic nucleotide triphosphate regeneration after hypothermic reperfusion in the pig model: an in vitro P-NMR study," *Transplantation*, Sep. 1996; 62 (6): 787-793.

Upadhya et al., "Evidence that actin disassembly is a requirement for matrix metalloproteinase secretion by sinusoidal endothelial cells during cold preservation in the rat," *Hepatology*, Jul. 1999; 30 (1): 169-176.

Lemasters et al., "Reperfusion injury after liver preservation for transplantation," *Annu Rev Pharmacol Toxicol*, 1997; 37: 327-338.

Arii et al., "Liver transplantation and hepatic sinusoidal cells," *J Gastroenterol Hepatol*, 1995; 10 Supp 1: S92-S6.

Arai et al., "Protection of sinusoidal endothelial cells against storage/reperfusion injury by prostaglandin E2 derived from Kupffer cells," *Transplantation*, Aug. 1999; 68 (3): 440-445.

Jamieson et al., "The 24- to 48-hour preservation of canine liver by simple cold storage using UW lactobionate solution," *Transplant Proc*, Feb. 1989; 21 (1 Pt 2): 1292-1293.

Merion et al., "A prospective controlled trial of cold-storage versus machine-perfusion preservation in cadaveric renal transplantation," *Transplantation*, Aug. 1990; 50 (2): 230-233.

Matsuno et al., "The effect of machine perfusion preservation versus cold storage on the function of kidneys from non-heart-beating donors," *Transplantation*, Jan. 1994; 57 (2): 293-294.

Changani et al., "Non-invasive assessment of ATP regeneration potential of the preserved donor liver. A 31P MRS study in pig liver," *J Hepatol*, 1997; 26 (2): 336-342.

Schon et al., "Liver transplantation after organ preservation with normothermic extracorporeal perfusion," *Ann Surg*, Jan. 2001; 233 (1): 114-123.

Imber et al., "Advantages of normothermic perfusion over cold storage in liver preservation," *Transplantation*, Mar. 2002, 73 (5): 701-709.

Matsuno et al., "Liver transplantation from non-heart-beating donors: liver procurement without in situ portal flush," *Transplant Proc*, Feb. 1996; 28 (1): 203-204.

Lopez et al., "Histological changes during and after liver transplantation from non-heart-beating donor pig," *Transplant Proc*, 1997; 29 (8): 3471.

Fukunaga et al., "Endothelin antagonist improves viabiity of liver grafts from non-heart-beating donors," *Transplant Proc*, 1999; 31 (1-2): 460-461.

Tojimbara et al., "Liver transplantation from non-heart beating donors in rats: influence of viscosity and temperature of initial flushing solutions on graft function," *Liver Transpl Surg*, Jan. 1997; 3 (1): 39-45.

Takada et al., "Hepatic allograft procurement from non-heart-beating donors: limits of warm ischemia in porcine liver transplantation," *Transplantation*, Feb. 1997; 63 (3): 369-373.

Valero et al., "L-arginine reduces liver and biliary tract damage after liver transplantation from non-heart-beating donor pigs," *Transplantation*, Sep. 2000; 70 (5): 730-737.

Igea et al., "Indocyanine green clearance as a marker of graft function in liver transplantation," *Transplant Proc*, 1999; 31 (6): 2447-2448.

Krenn et al., "Detection of graft nonfunction after liver transplantation by assessment of indocyanine green kinetics," *Anesth Analg*, 1998; 87 (1): 34-36.

Jalan et al., "A pilot study of indocyanine green clearance as an early predictor of graft function," *Transplantation*, Jul. 1994; 58 (2): 196-200.

Itasaka et al., "Serum hyaluronic acid for the assessment of graft viability in porcine liver transplantation," *Surg Today*, 1994; 24 (8): 719-724.

Itasaka et al., "Significance of hyalurnonic acid for evaluation of hepatic endothelial cell damage after cold preservation/reperfusion," *J Surg Res*, Nov. 1995; 59 (5): 589-595.

Reinders et al., "Hyaluronic acid uptake in the assessment of sinusoidal endothelial cell damage after cold storage and normothermic of rate livers," *Transpl Int*, 1996; 9 (5): 446-453.

Sudo et al., "Assessment of graft viability using hyaluronic acid and adenosine triphosphate in orthotopic liver transplantation from non-heart-beating donors," *Transplant Proc*, 2000; 32 (7): 2114-2115.

Abdennebi et al., "Evaluation of parenchymal and nonparenchymal cell injury after different conditions of storage and reperfusion," *Transpl Int*, 1998; 11 (5): 365-372.

Upadhya et al., "Effect of cold preservation on intracellular calcium concentration and calpain activity in rat sinusoidal endothelial cells," *Hepatology*, Feb. 2003; 37 (2): 313-323.

Rauen et al., "Cold-induced apoptosis in cultured hepatocytes and liver endothelial cells: mediation by reactive oxygen species," *FASEB J*, Jan. 1999; 13 (1): 155-168.

Net et al., "Hepatic xanthine levels as viability predictor of livers procured from non-heart-beating donor pigs," *Transplantation*, May 2001; 71 (9): 1232-1237.

Mitchell et al., "Effects of different cold preservation solutions on restoration of hepatic energy metabolism during cold reperfusion," *Cryobiology*, 1996: 33 (4): 413-422.

Gonzelez et al., "Predictive factors of early postoperative graft function in human liver transplantation," *Hepatology*, Sep. 1994; 20 (3): 565-572.

Gonzelez et al., "Adenine nucleotide liver tissue concentrations from non-heart-beating donor pigs and organ viability after liver transplantation," *Transplant Proc*, 1997; 29 (8): 3480-3481.

Adham et al., "The isolated perfused porcine liver: assessment of viability during and after six hours of perfusion," *Transpl Int*, 1997; 10 (4): 299-311.

Lee et al., "Heterogeneous flow patterns during hypothermic machine perfusion preservation of livers," *Transplantation*, Dec. 2000; 70 (12): 1797-1802.

Belzer et al., "A new perfusate for kidney preservation," *Transplantation*, 1982; 33 (3): 322-323.

COMPOSITION AND METHOD FOR THE RESTORATION AND PRESERVATION OF TRANSPLANT ORGANS PROCURED FROM DCD DONORS

CROSS-REFERENCE TO RELATED APPLICATIONS

The present application claims the benefit of U.S. Provisional Application No. 60/702,597, filed Jul. 27, 2005, and U.S. Provisional Application No. 60/739,886, filed Nov. 28, 2005, the contents of which are both incorporated by reference in their entirety.

FIELD OF THE INVENTION

The invention relates generally to a method and solution for preserving organs for transplantation, and more particularly to a solution and a method for extending the transplantation viability of an organ recovered from a Donation After Cardiac Death (DCD) donor.

BACKGROUND OF THE INVENTION

According to the United Network for Organ Sharing (UNOS), there are more than 92,000 individuals in the United States on the organ transplant waiting list as of June 2006. The number of people of the waiting list continues to increase every year. However, the number of available deceased organs has remained about the same. The result is a shortage of organs and a longer time on the wait list. UNOS has reported that approximately 6,500 transplant candidates died in 2005 while awaiting an organ transplant. Each day approximately 17 people die while waiting for a transplant of a vital organ, such as a heart, liver, kidney, pancreas, lung or bone marrow. A primary cause of the long wait times is the lack of available organs for transplant.

Today, the primary source of transplant organs is from cadaveric donors, also referred to as heart beating donors (HBD). Heart beating donors are donors that have been clinically declared brain dead and who are being maintained on life support. Transplants from non-beating heart donors, also referred to as DCD donors, are procured after cessation of cardiopulmonary function in the donor, and can occur in a controlled setting, after a planned withdrawal of life support, or in an uncontrolled situation with the onset of sudden cardiac arrest.

Traditionally, DCD organs have not been widely accepted for transplantation because of ethical and medical concerns. The major ethical issues involving DCD organs focused on whether the procurement of DCD organs violated the "dead-donor rule" in that the retrieval of organs for transplantation does not cause the death of a donor. With the acceptance of cardiopulmonary criterion for determining the death of the prospective organ donor, the ethical issues associated with DCD organs have largely been resolved. Based on a cardiopulmonary criterion, DCD donor death occurs when respiration and circulation have ceased and cardiopulmonary function will not resume spontaneously.

Medical concerns for the use of DCD organs have generally focused on the viability of organs recovered from DCD donors. Because DCD organs are not harvested until after the cessation of cardiopulmonary function, these organs are commonly associated with injury that results from warm ischemia. Warm ischemia is characterized by a decrease or complete stop of blood flow to one or several organs. It is generally believed that organs that have been exposed to warm ischemia for periods approaching 30 minutes are not suitable for transplantation. For instance, studies have shown that increased warm ischemia time in livers results in increases in cellular injury, ATP deprivation, and microvascular thrombosis, which can result in impairments in hepatic function upon reperfusion. Injury in DCD organs can also result from reperfusion, which refers to the restoration of blood flow to the organs. Studies have shown that ischemia followed by reperfusion induces apoptosis and inflammation that can cause tissue damage and organ dysfunction, which is called ischemia-reperfusion (I/R) injury or reperfusion injury. Ischemia-reperfusion injury accompanying organ transplantations can result in dysfunction of the transplanted organ and in some cases, death of the patient.

Cold preservation has been shown to help reduce injuries associated with ischemia and improve the viability of transplant organs. The main purpose of cold preservation is to suppress metabolic and proteolytic activities during storage so that the organ may remain viable for transplantation over a longer period of time. Generally, there are two primary forms of cold preservation. Simple cold storage is the most common and involves flushing the blood out of the organ and infusing it with a cold preservation solution. The second method is hypothermic machine perfusion (HMP) and involves continuous perfusion of the organ with a perfusate maintained at a temperature between 4° C. and 8° C. Conventionally, perfusion is done at low pressure and usually with the pulsatile flow of about 0.6 to 10 ml/min/g of tissue.

Several preservation solutions aiming at minimizing tissue damage in the organ transplants during hypothermal storage have been developed. One such solution, which is commonly referred to as the University of Wisconsin (UW) solution, has been shown to be effective for reducing reperfusion injury in kidneys obtained from BHD donors. The UW solutions are described in greater detail in U.S. Pat. Nos. 4,798,824 and 4,879,283. While the UW solution and some other preservation solutions, such as the Euro-Collins solution (Squifflet J. P. et al., Transplant. Proc. 13:693-696, 1981), have been effective in extending the cold preservation time of organs intended for transplantation, tissue injury during cold storage and particularly during reperfusion still occurs. Additionally, such solutions have not adequately addressed injuries that have occurred in DCD organs prior to perfusion of the preservation solution as a result of warm ischemia. As a result, DCD organs, such as the liver and pancreas, may still not be suitable for transplantation.

Thus, there exists a need for a solution and a method for improving the viability of organs recovered from DCD donors.

BRIEF SUMMARY OF THE INVENTION

The present invention provides a perfusion solution comprising specific metabolic agents, antioxidant agents, and membrane stabilizer agents that can help improve preservation, organ viability, and in some cases recover organs that would otherwise being unusable for transplantation. As a result, marginal donor organs, such as DCD organs, can be used in transplant operations.

In a further embodiment, the perfusion solution can be used in combination with hypothermic machine perfusion. It has been found that combination of the perfusion solution and hypothermic machine perfusion can help prevent or reduce further damage to the organ and restore the organ's antioxidant system, stabilize the cellular cytoskeleton and cellular membranes, inhibit arachidonic acid pathway, provide oncotic support, reduce interstitial edema formation, and help restore energy stores within the organ. As a result, the method can be used to improve the viability of otherwise marginal donor organs. In addition to restoring viability, the invention may also help improve the length of preservation time between removal of the organ from the donor and transplantation. As a result, transplantation viability can be further improved by permitting more time to match the donor organ to the most appropriate recipient.

In one embodiment, the present invention provides a perfusion solution and method that can be used to reclaim and preserve DCD livers. As a result, the organ donor pool can be significantly expanded, which can potentially increase the number of transplants per year and reduce the length of time a patient must spend on the waiting list. Thus, the invention overcomes many of the problems discussed above with respect to DCD organs.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 1 is a schematic illustration of a HMP system that can be used to circulate a perfusion system through a liver.

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The present invention is directed to new solutions and method for restoring and preserving organs that have been recovered from DCD donors. Suitable organs on which the solutions of this invention may be used include, for example, liver, kidney, and pancreas, and in particular the liver. In a further aspect, the present invention provides a method that helps to improve organ viability and restore organ function. As a result, marginal donors, such as those recovered from DCD donors may be used in transplant operations.

As discussed in greater detail below, the Applicants have discovered that organ viability and function can be improved and in some cases recovered by perfusing the organ with a perfusion solution comprising specific metabolic agents, antioxidant agents, and membrane stabilizers in combination with hypothermic machine perfusion. It has been found that combination of the perfusion solution and hypothermic machine perfusion can help prevent or reduce further damage to the organ and restore the organ's anti-oxidant system, stabilize the cellular cytoskeleton and cellular membranes, inhibit arachidonic acid pathway, provide oncotic support, reduce interstitial edema formation, and help restore energy stores within the organ. As a result, the method can be used to improve the viability of otherwise marginal donor organs. In addition to restoring viability, the invention may also help improve the length of preservation time between removal of the organ from the donor and transplantation. As a result, transplantation viability can be further improved by permitting more time to match the donor organ to the most appropriate recipient.

The individual components of the inventive perfusion solution are all nontoxic and have been found to be stable during storage. While some of the components of the present invention are similar to those of other known preservation solutions, it has surprisingly been found that the addition of specific metabolic support agents, antioxidant agents, and membrane stabilizers in combination with hypothermic machine perfusion can be used to reduce damage associated with warm ischemia and increases organ viability for extended periods of time. In particular, it has been discovered the inventive composition in combination with hypothermic machine perfusion can be used to restore liver organs that would be otherwise considered marginal so that they are viable for transplantation. In some embodiments, the perfusion solution of the invention may be used in the same manner and for the same tissues and organs as known machine perfusion solutions.

The inventive perfusion solution is designed to prevent various mechanisms which cause injury to the organ and to reverse damage that can result from warm ischemia, and thus must be a composition that (1) prevents or restricts intracellular acidosis, (2) stabilizes the cellular cytoskeleton and cellular membranes, (3) prevents injury from oxygen-derived free radicals, especially during reperfusion, (4) sustains appropriate metabolic requirement and enables the regeneration of high-energy phosphate compounds during perfusion, and (5) prevents the rapid changes in intracellular $Na^+$—$H^+$—$Ca^{++}$ following reperfusion. In one embodiment, the solution of the present invention comprises a modified form of the UW solution comprising the addition of specific metabolic agents, antioxidant agents, and membrane stabilizers. In one embodiment, the modified UW solution may also include starch. In a further embodiment, a modified form of the UW solution is provided in which there is substantially no starch present. An exemplary form of the modified UW solution is described in Table 1 below.

TABLE 1

| Concentration Ranges in 1 Liter | |
|---|---|
| lactobionate | 90 mM to 110 mM |
| Potassium | 90 mM to 110 mM |
| Sodium | 20 mM to 30 mM |
| adenosine | 0.5 mM to 10 mM |
| magnesium sulphate | 4 mM to 15 mM |
| potassium phosphate, e.g., $KH_2PO_4$ | 15 mM to 30 mM |
| raffinose | 25 mM to 35 mM |
| allopurinol | 0.5 mM to 4 mM |
| glutathione | 1 mM to 10 mM |
| metabolic support agent | 0.5 mM to 10 mM |
| membrane stabilizer | 0.5 mM to 10 mM |
| antioxidant agent | 0.1 mM to 10 mM |

The perfusion solution of the present invention includes one or more metabolic support agents that can help restore energy stores in the organ that have become severely depressed as a result of warm ischemia. The Applicants of the present invention have discovered that the solution in combination with HMP can help restore energy stores and mitochondrial function in the cells, which can lead to sustainable ATP production following transplantation. Suitable metabolic support agents that may be used include, for example, glucose, glutamine, lactate, pyruvate, lysine, and combinations thereof. The metabolic support agents may be present in an amount from about 0.1 mM to 10 mM, and in particular in an amount between about 1 mM to 5.5 mM.

In addition to allopurinol and glutathione, the perfusion solution of the invention further comprises one or more additional antioxidant agents such as beta-carotene, catalase, superoxide dismutase, dimethyl thiourea (DMTU), diphenyl phenylene diamine (DPPD), mannitol, cyanidanol, α-tocopherol, desferoxamine, 6-hydroxy-2,5,7,8-tetramethyl chroman-2-carboxylic acid, which is available under the tradename Trolox, or N-acetyl cysteine, or combinations thereof, in an amount effective to inhibit the generation of oxygen-derived free radicals. In a preferred embodiment, the perfusion includes an antioxidant agent selected from the group consisting of selected from the group consisting of α-tocopherol, desferoxamine, 6-hydroxy-2,5,7,8-tetramethyl chroman-2-carboxylic acid, and N-acetyl cysteine. In one embodiment, the additional antioxidant is a combination of N-acetyl cysteine, desferoxamine, and 6-hydroxy-2,5,7,8-tetramethyl chroman-2-carboxylic acid. The antioxidants are generally present in an amount from about 0.1 mM to 10 mM depending upon the potency of the particular antioxidant.

Suitable membrane stabilizers that may be used in the present invention include, for example, calcium, glycine, chlorpromazine, and combinations thereof. Membrane stabilizers help to improve the selective permeability and stability of cell membranes which helps improve the ability to maintain ionic balance.

In addition to the above described components, the perfusion solution may also include oncotic support agents, such as pentastarch, dextran, polyethylene glycol, and albumin. When present, the amount of oncotic support agents in the perfusion solution is about 0.1 to 160 mM, and in particular between 10 to 100 mM. In some embodiments, the solution may include one or more vascular support agents, such as vasodilators, e.g., nitric oxide donors or prostacyclin.

In a preferred embodiment, the profusion solution, includes but is not limited to:

TABLE 2

| Concentration Ranges in 1 Liter | |
|---|---|
| lactobionate | 90 mM to 110 mM |
| Potassium | 90 mM to 110 mM |
| Sodium | 20 mM to 30 mM |
| adenosine | 0.5 mM to 10 mM |
| magnesium sulphate | 4 mM to 15 mM |
| potassium phosphate, e.g., KH$_2$PO$_4$ | 15 mM to 30 mM |
| raffinose | 25 mM to 30 mM |
| allopurinol | 0.5 mM to 4 mM |
| glutathione | 1 mM to 10 mM |
| Glycine | 1 mM to 10 mM |
| Trolox C | 100 µM to 1 mM |
| N-acetyl L-cysteine | 1 mM to 10 mM |
| Desferal (Deferoxamine) | 0.1 mM to 1 mM |
| L-Glutamine | 0.5 mM to 5 mM |
| Glucose | 1 mM to 10 mM |
| CaCl$_2$ | 0.5 mM to 5 mM |

In a more preferred embodiment, the perfusion solution includes the following composition:

TABLE 3

| Concentration Ranges in 1 Liter | |
|---|---|
| lactobionate | Approx. 100 mM |
| Potassium | Approx. 100 mM |
| Sodium | Approx. 25 mM |
| adenosine | Approx. 5 mM |
| magnesium sulphate | Approx. 5 mM |
| potassium phosphate, e.g., KH$_2$PO$_4$ | Approx. 25 mM |
| raffinose | Approx. 30 mM |
| allopurinol | Approx. 1 mM |
| glutathione | Approx. 3 mM |
| Glycine | Approx. 5 mM |

TABLE 3-continued

| Concentration Ranges in 1 Liter | |
|---|---|
| Trolox C | Approx. 200 µM |
| N-acetyl L-cysteine | Approx. 5 mM |
| Desferal (Deferoxamine) | Approx. 0.25 mM |
| L-Glutamine | Approx. 2 mM |
| Glucose | Approx. 5.5 mM |
| CaCl$_2$ | Approx. 1 mM |

The invention also provides a method restoring the viability of an organ, such as the liver, in which the perfusion solution is used in combination with hypothermic machine perfusion. In one embodiment, the method includes pouring the perfusion solution into a chamber that mimics a deep hypothermic environment or physiological environment and moving the perfusion solution continuously through the chamber. The perfusion solution is infused in a mechanical fashion through the arterial or venous vascular system of cadaveric or living donor organs, or infused over or through a vascular biological substance in order to maintain organ or tissue viability during the ex vivo period. Perfusion temperatures may range from about 0° to about 10° C., and in particular between 0° and 7° C. in the hypothermic condition and are about 37° C., or room temperature, in the physiological condition. The perfusion solution remains in the vasculature of the organ as well as envelops the entire organ during the period of cold ischemia (i.e., hypothermic perfusion).

In some embodiments, the method may further include removing an organ from a donor that has suffered cardiac arrest; circulating the perfusion solution through the organ under hypothermic conditions (e.g., between 0° and 7° C.) for a sufficient amount of time to restore energy levels to the organ; rewarming the organ to physiological temperatures; and transplanting the organ into a recipient patient, such as a mammal in need. In a further embodiment, the method further includes the steps of removing an organ from a DCD donor; flushing the organ with a flush solution to remove any blood or residual cells; attaching the organ to an apparatus capable of performing hypothermic perfusion; introducing the perfusion solution into the organ, and circulating the perfusion solution through the organ for a sufficient amount of time to restore the viability of the organ for transplant.

In a further aspect of the invention, the Applicants have discovered that in addition to perfusing the organ with the perfusion solution, recovery of organ function can further be improved by the continuous administration of oxygen during hypothermic machine perfusion. In the recovering of livers, oxygenation can be provided through the portal vein by compressed air and equilibrated with the perfusion solution prior to introduction into the liver. In one embodiment the oxygen partial pressure in the perfusion solution may range from about 100 to 175 mmHg, and in particular between 150 to 175 mmHg. It is generally theorized that the combination of oxygen and the metabolite stabilizers helps the tissues of the organ to recover energy stores during perfusion.

Prior to circulating the perfusion solution, the organ can be flushed with a solution to remove any blood or residual material from within the organ. Preferably, the flush solution has a concentration of K$^+$ ions similar to that of plasma (e.g., about 4.5 mM), such as Krebs-Henseleit buffer solution or similar plasma-like salt solutions. It is believed that solutions having a K$^+$ concentration can result in vasoconstriction and poor flushout. After flushing is complete the organ is placed on the perfusion apparatus and cooled to preservation temperature over the course of 3 to 5 minutes by perfusion with cold flush solution. Once the organ is at hypothermic temperature, the organ can be perfused with the perfusion solution.

With reference to FIG. 1, a system for performing hypothermic machine perfusion on an organ, such as a liver is illustrated and broadly designated as reference number 10. The system includes a first circulation circuit for performing hypothermic machine perfusion, represented by the solid line, and a second circulation circuit for rewarming the organ, represented by the dashed line. The system includes a reservoir chamber 12 having a volume and internal dimensions that are configured and arranged to receive an organ 14 and a sufficient amount of perfusion solution to continuously circulate the perfusion solution through the organ.

In one embodiment, the HMP system includes a first circulation circuit having a first circulation path 16 and a second circulation path 18 that are in fluid communication with the perfusion solution in the chamber and with one or more veins/arteries of the organ. The system 10 also includes one or more pumps 20, such as a peristaltic pump, that can be used to controllably circulate the perfusion solution at a desired pressure. In some embodiments, the system also includes a plurality of filters 28 and air traps 30 for screening the perfusion solution as it is being continuously circulated through the system. The system also includes one or more heat exchanger/oxygenators 32 for introducing oxygen into the perfusion solution.

In the illustrated embodiment, the HMP system is adapted for the perfusion of a liver. In the case of a liver, circulation pathways 16, 18 can be connected to the hepatic artery and portal vein, respectively. Providing separate perfusion systems for the portal vein and hepatic artery helps to provide enhanced control, and hence, improved liver recovery during perfusion. Generally, the flow rate of the perfusion solution into the portal vein is between about 0.1 to 0.5 mL/min/g liver so that a pressure between 0.5 and 5 mmHg, and preferably less than 4 mmHg is maintained. The flow rate of the perfusion solution into the hepatic artery is typically between about 0.1 to 0.5 mL/min/g liver so that at a pressure between 20 and 40 mmHg, and preferably less than 25 mmHg is maintained.

In some embodiments, the HMP system may also include a second circulation circuit for rewarming the organ that includes additional circulation systems 24, 26. Preferably, the rewarming circuit has one or more pumps 22 that are separate and independent of the pumps 20 in the hypothermic circuit. It has generally been determined that a separate circuit for rewarming the liver provides enhanced control and improved recovery because the liver has different flow demands during perfusion and rewarming. In one embodiment, a main pump 22a will draw solution from the reservoir chamber 12 and pass the solution through the heat exchanger/oxygenator 32. A secondary pump 22b will draw off about 25% of this solution for the hepatic artery while the remaining 75% will be introduced into the portal vein of the liver. In this embodiment, both portal vein and hepatic artery will be oxygenated. For example, during rewarming flow rate through the portal vein may be maintained at a rate of about 2-3.5 mL/min/g of liver and through the hepatic artery at about 0.5 to 1 mL/min/g of liver.

In the illustrated embodiment, the heat exchanger/oxygenator 32 is disposed in line with the portal vein circulation pathway 18. Since the portal vein provides about 75% of the liver's circulation, oxygenating the portal vein perfusate should provide sufficient $O_2$ to meet the needs of the liver. However, an additional oxygenator can be added to the hepatic artery circulation pathway 16 if desired.

The following examples are provided to further illustrate the present invention and are not to be construed as limiting the invention in any manner.

EXAMPLE 1

A perfusion solution having the following composition was prepared by 1) preparing a liter of UW solution, available from DuPont under the tradename Viaspan™, in which the starch and gluthione were omitted. The solution was filtered and stored at 4° C. 2) A second stock solution comprising of 0.2 mM OKY46 thromboxane $A_2$ inhibitor, available from Calbiochem in DMSO was prepared and stored at −20° C. 3) The following ingredients were then added to the UW solution prepared in step 1).

| Glycine | 5 mM |
| Trolox C | 200 µM |
| N-acetyl L-cysteine | 5 mM |
| Desferal (Deferoxamine) | 0.25 mM |
| L-Glutamine | 2 mM |
| Glucose | 5.5 mM |
| $CaCl_2$ | 1 mM |
| L-Glutathione | 3 mM |

1 mL of the stock solution prepared in step 2) was added to the modified UW solution with stirring for about 5 minutes. The pH of the solution was adjusted to 7.4 using 4:1 ratio of 5M-KOH and 5M NaOH. The resulting solution was stored at 4° C. unit use.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A solution for the preservation and restoration of organ function, the solution comprising, per liter of solution:
    a) from about 15 to 30 mM of potassium phosphate;
    b) from about 1 to 10 mM of glutathione;
    c) from about 0.5 to 10 mM of adenosine;
    d) from about 90 to 110 mM of lactobionate;
    e) from about 15 to 30 mM of sodium;
    f) from about 90 to 110 mM of potassium;
    g) from about 0.5 to 4 mM of allopurinol;
    h) from about 0.1 to 10 mM of at least one antioxidant agent in addition to glutathione and allopurinol;
    i) from about 0.5 to 10 mM of a metabolic support agent; and
    j) from about 0.5 to 10 mM of a membrane stabilizer selected from the group consisting of calcium, glycine, chlorpromazine, and combinations thereof.

2. The solution of claim 1, wherein said antioxidant agent is selected from the group consisting of α-tocopherol, deferoxamine, 6-hydroxy-2,5,7,8-tetramethyl chroman-2-carboxylic acid, and N-acetyl cysteine.

3. The solution of claim 1, wherein said antioxidant agent comprises a combination of N-acetyl cysteine, deferoxamine, and 6-hydroxy-2,5,7,8-tetramethyl chroman-2-carboxylic acid.

4. The solution of claim 1, wherein said metabolic support agent is selected from the group consisting of glucose, glutamine, and combinations thereof.

5. The solution of claim 1, wherein said metabolic support agent comprises from about 0.5 mM to 5 mM of glutamine and about 1 mM to 10 mM of glucose.

6. The solution of claim 1, wherein said metabolic support agent comprises about 2 mM of glutamine and about 5.5 mM of glucose.

7. The solution of claim 1, wherein said membrane stabilizer comprises from about 1 mM to about 10 mM of glycine, from about 1 mM to 5 mM of $CaCl_2$.

8. The solution of claim 1, wherein the solution comprises:
   a) about 5 mM of glycine
   b) about 5 mM of N-acetyl L-cysteine;
   c) about 0.25 mM of deferoxamine;
   d) about 2 mM of L-glutamine;
   e) about 1 mM of $CaCl_2$; and
   g) about 5.5 mM glucose.

9. The solution of claim 1, further comprises an oncotic support agent selected from the group consisting of dextran, polyethylene glycol, albumin, pentastarch, and combinations thereof.

10. A solution for the preservation and restoration of organ function, the solution comprising, per liter of solution:
    a) about 100 mM of lactobionate;
    b) about 100 mM of potassium;
    c) about 25 mM of sodium;
    d) about 25 mM of potassium phosphate;
    e) about 5 mM of magnesium sulphate;
    f) about 30 mM of raffinose
    g) about 1 mM of allopurinol
    h) about 3 mM of glutathione;
    i) about 5 mM of adenosine;
    j) about 5 mM of glycine
    k) about 5 mM of N-acetyl L-cysteine;
    l) about 0.25 mM of deferoxamine;
    m) about 2 mM of L-Glutamine;
    n) about 1 mM of $CaCl_2$;
    o) about 200 μM of 6-hydroxy-2,5,7,8-tetramethyl chroman-2-carboxylic acid; and
    p) about 5.5 mM glucose.

11. A solution for the preservation and restoration of organ function, the solution comprising, per liter of solution:
    a) from about 15 to 30 mM of potassium phosphate;
    b) from about 1 to 10 mM of glutathione;
    c) from about 0.5 to 10 mM of adenosine;
    d) from about 90 to 110 mM of lactobionate;
    e) from about 15 to 30 mM of sodium;
    f) from about 90 to 110 mM of potassium;
    g) from about 0.5 to 4 mM of allopurinol;
    h) from about 0.1 to 10 mM of at least one antioxidant agent in addition to glutathione and allopurinol;
    i) from about 0.5 to 10 mM of a metabolic support agent comprising up to about 5 mM of glutamine and about 1 mM to 10 mM of glucose; and
    j) from about 0.5 to 10 mM of a membrane stabilizer.

12. The solution of claim 11, wherein said metabolic support agent comprises about 2 mM of glutamine and about 5.5 mM of glucose.

13. The solution of claim 11, wherein said membrane stabilizer is selected from the group consisting of calcium, glycine, chlorpromazine, and combinations thereof.

14. The solution of claim 11, wherein said membrane stabilizer comprises from about 1 mM to about 10 mM of glycine, from about 1 mM to 5 mM of $CaCl_2$.

15. The solution of claim 11, wherein the solution comprises:
    a) about 5 mM of glycine
    b) about 5 mM of N-acetyl L-cysteine;
    c) about 0.25 mM of deferoxamine;
    d) about 2 mM of L-glutamine;
    e) about 1 mM of $CaCl_2$; and
    g) about 5.5 mM glucose.

16. A solution for the preservation and restoration of organ function, the solution comprising, per liter of solution:
    a) from about 15 to 30 mM of potassium phosphate;
    b) from about 1 to 10 mM of glutathione;
    c) from about 0.5 to 10 mM of adenosine;
    d) from about 90 to 110 mM of lactobionate;
    e) from about 15 to 30 mM of sodium;
    f) from about 90 to 110 mM of potassium;
    g) from about 0.5 to 4 mM of allopurinol;
    h) from about 0.1 to 10 mM of an additional antioxidant agent selected from the group consisting of α-tocopherol, deferoxamine, 6-hydroxy-2,5,7,8-tetramethyl chroman-2-carboxylic acid, and N-acetyl cysteine;
    i) from about 0.5 to 10 mM of a metabolic support agent; and
    j) from about 0.5 to 10 mM of a membrane stabilizer.

* * * * *